US012623937B2

(12) United States Patent
Dinamarca et al.

(10) Patent No.: US 12,623,937 B2
(45) Date of Patent: May 12, 2026

(54) BIOELECTROCHEMICAL BIOREACTOR

(71) Applicant: Universitetet i Sørøst-Norge, Borre (NO)

(72) Inventors: Carlos Antonio Saldias Dinamarca, Stathelle (NO); Rune Bakke

(73) Assignee: Universitetet i Sørøst-Norge, Borre (NO)

( * ) Notice: Subject to any disclaimer, the term of this patent is extended or adjusted under 35 U.S.C. 154(b) by 747 days.

(21) Appl. No.: 17/925,647

(22) PCT Filed: May 18, 2021

(86) PCT No.: PCT/EP2021/063085
§ 371 (c)(1),
(2) Date: Nov. 16, 2022

(87) PCT Pub. No.: WO2021/233880
PCT Pub. Date: Nov. 25, 2021

(65) Prior Publication Data
US 2023/0312381 A1 Oct. 5, 2023

(30) Foreign Application Priority Data
May 18, 2020 (EP) .................................... 20175145

(51) Int. Cl.
*C02F 3/00* (2023.01)
*C12P 5/02* (2006.01)
(Continued)

(52) U.S. Cl.
CPC ............... *C02F 3/005* (2013.01); *C12P 5/02* (2013.01); *C12P 5/023* (2013.01); *C25B 1/50* (2021.01);
(Continued)

(58) Field of Classification Search
CPC ... C02F 3/005; C25B 1/50; C25B 3/03; C25B 3/25; C25B 3/26
See application file for complete search history.

(56) References Cited

U.S. PATENT DOCUMENTS

2011/0177564 A1* 7/2011 Stephanopoulos ....... C12P 7/16
435/162
2012/0100590 A1 4/2012 Tartakovsky et al.
(Continued)

FOREIGN PATENT DOCUMENTS

WO 2011-000084 A1 1/2011
WO WO-2012011984 A1 * 1/2012 ............. C02F 3/005
WO WO-2020053529 A1 * 3/2020 ............. C02F 3/005

OTHER PUBLICATIONS

Mehta et al. "Electricity generation from carbon monoxide in a single chamber microbial fuel cell" Enzyme and Microbial Technology 46 (2010) 450 (Year: 2010).*
(Continued)

*Primary Examiner* — Alexander W Keeling
*Assistant Examiner* — Alexander R. Parent
(74) *Attorney, Agent, or Firm* — Amster, Rothstein & Ebenstein LLP

(57) ABSTRACT

The present invention relates to a method for converting one or more influent streams comprising organic compounds present in an aqueous liquid stream such as wastewater and optionally inorganic carbon compounds into an effluent stream comprising short chain organic molecules in a bioreactor comprising electrodes, said method comprising: • the electrochemical oxidation of said organic compounds, thereby forming inorganic carbon compounds; and; • the electrochemical of said inorganic compound such as ammonium, ammonia and sulfides present in an aqueous liquid stream entering the bioreactor. • the bio-electrochemical reduction of said inorganic carbon compounds, thereby
(Continued)

forming short chained organic molecules (such as methane); characterized in that said bioreactor is an anaerobic bioreactor comprising a biofilm growing on the cathodes and optionally the anodes as well as microorganism in suspension.

12 Claims, 3 Drawing Sheets

(51) Int. Cl.

| | | |
|---|---|---|
| *C25B 1/50* | (2021.01) | |
| *C25B 3/03* | (2021.01) | |
| *C25B 3/25* | (2021.01) | |
| *C25B 3/26* | (2021.01) | |

(52) U.S. Cl.
CPC .................. *C25B 3/03* (2021.01); *C25B 3/25* (2021.01); *C25B 3/26* (2021.01); *C02F 2201/46135* (2013.01); *C02F 2209/03* (2013.01); *C02F 2209/04* (2013.01)

(56) References Cited

U.S. PATENT DOCUMENTS

| | | | |
|---|---|---|---|
| 2013/0299400 A1 | 11/2013 | Silver et al. | |
| 2014/0206066 A1* | 7/2014 | Datta ........................ | C12P 7/16 |
| | | | 435/252.7 |
| 2021/0170357 A1* | 6/2021 | Kumar ...................... | C25B 9/07 |
| 2021/0340039 A1* | 11/2021 | Moreau ..................... | C25B 9/63 |

OTHER PUBLICATIONS

Guo et al. "Efficient Methane Production from Beer Wastewater in a Membraneless Microbial Electrolysis Cell with a Stacked Cathode: The Effect of the Cathode/Anode Ratio on Bioenergy Recovery" Energy Fuels 2017, 31, 615-620 (Year: 2017).*

Liu et al. "Membrane installation for enhanced up-flow anaerobic sludge blanket (UASB) performance" Journal of Bioscience and Bioengineering 116(3) 357 2013 (Year: 2013).*

International Search Report and Written Opinion dated Aug. 20, 2021 issued in PCT International Patent Appln. No. PCT/EP2021/063085.

Escapa et al., "Microbial Electrolysis Cells: An Emerging Technology for Wastewater Treatment and Energy Recovery. From Laboratory to Pilot Plant and Beyond," Renewable and Sustainable Energy Reviews, vol. 55, 2016, available online Dec. 5, 2015, pp. 942-956.

Guo et al., "Efficient Methane Production From Beer Wastewater in a Membraneless Microbial Electrolysis Cell With a Stacked Cathode: The Effect of the Cathode/Anode Ratio on Bioenergy Recovery," Energy & Fuels, vol. 31, 2017, published Dec. 12, 2016, pp. 615-620.

Bo et al., "A New Upgraded Biogas Production Process: Coupling Microbial Electrolysis Cell and Anaerobic Digestion in Single-Chamber, Barrel-Shape Stainless Steel Reactor," Electrochemistry Communications, vol. 45, 2014, available online May 28, 2014, pp. 67-70.

Enzmann et al., "Methanogens: Biochemical Background and Biotechnological Applications," AMB Express, vol. 8, No. 1, 2018, pp. 1-22.

Second Written Opinion dated Apr. 1, 2022 issued in PCT International Patent Appln. No. PCT/EP2021/063085.

Leonzio, "Power to Gas Systems Integrated With Anaerobic Digesters and Gasification Systems," Waste and Biomass Valorization, vol. 12, 2021, published online Dec. 5, 2019, pp. 29-64.

International Preliminary Report on Patentability dated Jul. 13, 2022 issued in PCT International Patent Appln. No. PCT/EP2021/063085.

Sivalingam et al., "Integrating Syngas Fermentation Into a Single-Cell Microbial Electrosynthesis (MES) Reactor," Catalysts, vol. 11, No. 40, 2021, published Dec. 31, 2020, https://doi.org/10.3390/catal11010040, pp. 1-10.

Summons to attend oral proceedings pursuant to Rule 115(1) EPC, Dated Dec. 3, 2012 (Dec. 3, 2012), Issued in EP Application No. 21724178.5.

Sónia G. Barbosa et al: "Bioelectrochemical systems (BESs) towards conversion of carbon monoxide/syngas: A mini-review", Renewable and Sustainable Energy Reviews, vol. 135, No. 110358, (2021), Published online Sep. 25, 2020 (Sep. 25, 2020), 10 pages.

P. Mehta et al: "Electricity generation from carbon monoxide in a single chamber microbial fuel cell", Enzyme and Microbial Technology (2010), vol. 46, pp. 450-455.

* cited by examiner

BIOELECTROCHEMICAL BIOREACTOR

CROSS-REFERENCE TO RELATED APPLICATIONS

This application is a U.S. national stage entry under 35 U.S.C. § 371 of PCT International Patent Application No. PCT/EP2021/063085, filed May 18, 2021, which claims priority to European Patent Application No. 20175145.0, filed May 18, 2020, the contents of each of which are incorporated herein by reference in their entirety.

FIELD OF THE INVENTION

The present invention relates to the field of organic slurries and wastewater treatment systems. More specifically, the present invention relates to the conversion of one or more influent streams comprising organic compounds present in an aqueous liquid stream and optionally inorganic carbon compounds, into one or more effluent stream(s) comprising short chain organic molecules in a bioreactor comprising electrodes, said method comprising both the bio-electrochemical reduction of inorganic carbon compounds to form short chained organic molecules and the electrochemical and/or the bio-electrochemical oxidation of organic and/or inorganic compounds.

BACKGROUND OF THE INVENTION

Global society is moving out from a dependent fossil fuel base economy towards more renewable, non-fossil based fuels. Carbon base materials, chemicals and transportation fuels are for the most part made from fossil resources and there is no sufficiently efficient industrial technology for non-fossil based production immediately available. There is also an urgent need to reduce greenhouse emissions associated with fossil fuel consumption.

The demand for alternatives such as renewable methane gas is expected to have a steady growth as more liquefied biomethane is used in both land bases and maritime heavy transport. The amount of available organic waste alone will not suffice the growing market which targets the use of fuels from recyclable organic sources. In Europe biogas is today mainly used for heating, electricity generation and transport fuel. The share of biogas used as transport fuels is higher in Scandinavian countries because local public (communal) transportation is increasingly done by vehicles that run on upgraded biogas. Several land based heavy transport companies and truck producers have also engaged in the use and production of machines running of liquefied biogas. The composition of biogas may vary with typical between 30-50% $CO_2$, 70-50% methane and 350-10000 ppm $H_2S$. In order for the biogas to be used it needs to be further upgraded (e.g. removing $CO_2$ and $H_2S$) using technologies such as amine scrubbers. These upgrading processes are generally energy intensive and use chemicals such as amines and alkali solutions that in turn need to be removed in downstream processes.

European legislation strongly discourages both the transport and deposition of sludge's in open fields. This has been the preferred solution of e.g. biogas plants where after the process of anaerobic digestion the remaining sludge is driven away to farmland to be used as a fertilizer. However new research and public awareness have given light to the dangers of spreading microplastics and other chemicals in the fields because much of it ends up in waterbodies due to runoff. Another negative aspect of this relates to the use of fossil fuel for transporting the sludge over great distances, as such increasing the environmental burden. This creates a necessity to treat sludge of organic nature onsite. Recently, gasification or pyrolysis of organic sludge has become more common. During the gasification or pyrolysis organic sludge is converted into energy rich gasses, syngas, that comprises mainly of $CO_2$, $H_2$ and CO. Syngas can be transformed to other chemicals in a process known as syngas fermentation, which is a biological mediated process where $CO_2$, CO, $H_2$ gasses are converted to acids (e.g. acetic acid) and solvent (e.g. ethanol). This process is performed by a very metabolically diverse group of bacteria. This biological mediated process is however dominated by thermodynamic constrains. The concentration of acids and solvents reach a maximal concentration below the desired magnitude to make the volumetric production economically feasible.

In view of the above, there is a clear need to resolve at least some of the problems that currently restrict the use of biogas.

SUMMARY OF THE INVENTION

The inventors have now uncovered a process that allows for biogas upgrading as an electrochemical step that is integrated with anaerobic digestion for biogas production. For instance, with the methods and apparatuses described herein the methane content in biogas can be upgraded, e.g. to 80.0% or more, in particular to 85.0% or more, in particular to 90.0% or more, in particular 92.0% or more, more in particular 94.0% or more and more in particular 96.0% or more.

The present invention provides in a method for converting one or more influent streams comprising organic compounds present in an aqueous liquid stream and optionally inorganic carbon compounds, preferably C-1 inorganic carbon compounds such as $$CO_2, CO, HCO_3^-, \text{ and } CO_3^{2-},$$

into an effluent stream comprising short chain organic molecules, such as C1 to C4 hydrocarbons, C1 to C4 carboxylic acids and/or C1 to C4 aliphatic alcohols, in a biofilm bioreactor comprising electrodes, said method comprising:
  the electrochemical oxidation of said organic compounds, thereby forming inorganic carbon compounds; and;
  the bio-electrochemical reduction of said inorganic carbon compounds, thereby forming short chained organic molecules (such as methane or acetic acid);
characterized in that said bioreactor is an anaerobic bioreactor comprising a biofilm growing on the cathodes and optionally the anodes as well as microorganism in suspension.

More in particular the method as disclosed herein provides in a method for converting one or more influent streams comprising a wastewater stream comprising organic compounds and a gaseous or aqueous syngas stream comprising inorganic carbon compounds into an effluent stream comprising short chain organic C1 to C6 hydrocarbons or derivatives thereof in a single bioreactor comprising electrodes, said method comprising:
  the electrochemical oxidation of said organic compounds, thereby forming inorganic carbon compounds; and;
  the bio-electrochemical reduction of said inorganic carbon compounds, thereby forming short chained organic C1 to C6 hydrocarbons or derivatives thereof;

characterized in that said bioreactor is an anaerobic bioreactor comprising biofilms growing on the cathodes and optionally on the anodes as well as microorganisms in suspension.

More in particular the method as disclosed herein provides in that said single bioreactor is a single chamber bioreactor not comprising a membrane to divide the bioreactor in multiple chambers.

In a particular embodiment the method as described herein further comprises:

the bio-electrochemical oxidation of organic compounds, in particular using biological reactions with the microorganisms present in a biofilm on the anode;

the electrochemical oxidation of inorganic compounds, in particular the electrochemical oxidation of hydrogen sulfide and/or ammonium; and/or the bio-electrochemical oxidation of inorganic compounds, in particular the bio-electrochemical oxidation of hydrogen sulfide and/or ammonium.

In a particular embodiment the method as described herein in characterized in that said one or more influent streams of said bioreactor comprise an aqueous liquid stream, such as a wastewater stream, comprising organic compounds and a gaseous or aqueous syngas and/or carbon dioxide stream comprising inorganic carbon compounds.

In a particular embodiment the method as described herein in characterized in that said effluent stream of said bioreactor is biogas comprising methane.

In a particular embodiment the method as described herein in characterized in that said bioreactor is operated at a pressure above 1.0 bar and preferably below 3.0 bar.

In a particular embodiment the method as described herein in characterized in that said electrodes comprise of anodes and cathodes arranged in a surface area to volume ratio of at least 5 $m^2/m^3$, in particular at least 10 $m^2/m^3$, in particular at least 15 $m^2/m^3$ and in particular at least 20 $m^2/m^3$.

In a particular embodiment the method as described herein in characterized in that said electrodes comprise anodes and cathodes which are alternatingly stacked vertically or horizontally within said bioreactor.

In a particular embodiment the method as described herein further comprises the step of solubilizing the syngas and/or pre-fermenting the syngas with homoacetogenic bacteria prior to it entering into said bioreactor.

In a particular embodiment the method as described herein in characterized in that said bioreactor is an Up-flow Anaerobic Bed reactor, such as an Up-flow Anaerobic Sludge Bed (UASB) reactor.

In a particular embodiment the method as described herein in characterized in that the voltage applied to the electrodes for the electrochemical oxidation and bio-electrochemical reduction ranges between 250 mV and 1200 mV vs. the standard hydrogen electrode (SHE) at the cathode.

In a particular embodiment the method as described herein in characterized in that the suspension in the bioreactor is characterized by having a low oxidation reduction potential (ORP), preferably ranging between −250 and −450 mV.

In a particular embodiment the method as described herein further comprises the step of adding an aqueous nutrient solution to the influent.

In a further aspect, the present invention relates to a single anaerobic bioreactor for performing the method as described herein, comprising a biofilm growing on the cathodes and optionally the anodes as well as microorganisms in suspension, wherein said bioreactor is a stand-alone bioreactor or an add-on bioreactor to another bioreactor such as an existing anaerobic digester.

More in particular said bioreactor does not comprise a membrane to divide the bioreactor in multiple chambers In a particular embodiment the single bioreactor as described herein in characterized in that said bioreactor is an Up-flow Anaerobic Bed reactor, such as an Up-flow Anaerobic Sludge Bed (UASB) reactor. In a particular embodiment the bioreactor as described herein in characterized in that the electrodes comprise anodes and cathodes which are alternatingly stacked vertically or horizontally within said bioreactor.

In a further aspect, the present invention relates to the use of electrochemistry and microbial biological reactions in biofilm growing on the cathodes and optionally the anodes and microorganisms in suspension to convert one or more influent streams comprising organic compounds present in an aqueous liquid stream and optionally inorganic carbon compounds into an effluent stream comprising short chain organic molecules.

More in particular, the present invention relates to the use of electrochemistry and microbial biological reactions in biofilm growing on the cathodes and optionally the anodes and microorganisms in suspension to convert one or more influent streams comprising a wastewater stream comprising organic compounds and a gaseous or aqueous syngas stream comprising inorganic carbon compounds into an effluent stream comprising short chain organic C1 to C6 hydrocarbons or derivatives thereof.

BRIEF DESCRIPTION OF THE FIGURES

FIG. 1 shows a bioreactor with a horizontal arrangement of electrodes according to the present invention where the water flows from the bottom to the top. The reactor may also be operated in a horizontal position with a horizontal flow direction, or up-side-down or any angel in between.

Figure 1:
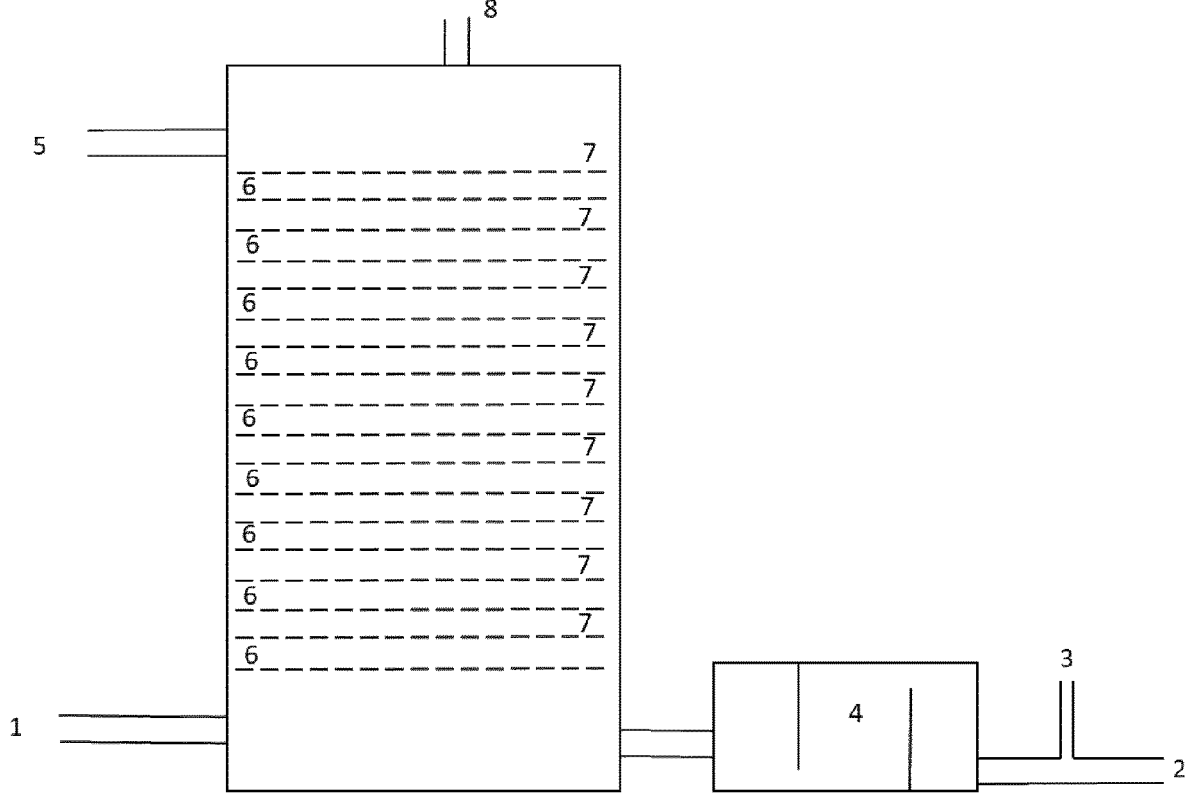

1-2 Influent stream (e.g. sludge/wastewater/slurry); 3 syngas input; 4 Short HRT fermenter/solubilization tank; 5 Effluent stream; 6 Cathode; 7 Anode; 8 Produced gas outlet.

DETAILED DESCRIPTION OF THE INVENTION

Before the present method and devices used in the invention are described, it is to be understood that this invention is not limited to particular methods, components, or devices described as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any method and material similar or equivalent to those described herein may be used in practice or testing of the present invention, the preferred methods and materials are now described.

In this specification and the appended claims, the singular forms "a", "an", "the" include both the singular and the plural, unless the context clearly indicates otherwise.

The terms "comprising", "comprises" and "comprised of" as used herein are synonymous with "including", "includes" or "containing", "contains", and are inclusive or open-ended and do not exclude additional, non-recited members, elements or method steps. Where this description refers to a product or process which "comprises" specific features, parts or steps, this refers to the possibility that other features, parts or steps may also be present, but may also refer to embodiments which only contain the listed features, parts or steps. The terms "comprising", "comprises" and "comprised of" also include the term "consisting of".

The enumeration of numeric values by means of ranges of figures comprises all values and fractions in these ranges, as well as the cited end points.

The terms "about" and "approximately" as used when referring to a measurable value, such as a parameter, an amount, a time period, and the like, is intended to include variations of +/−10% or less, preferably +/−5% or less, more preferably +1-1% or less, and still more preferably +/−0.1% or less, of and from the specified value, in so far as the variations apply to the invention disclosed herein. It should be understood that the value to which the term "about" or "approximately" refers per se has also been disclosed.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The inventors have now uncovered a single step process and single chamber bioreactor that allows for biogas upgrading. By combining electrochemical oxidation of organic compounds present in an aqueous liquid stream, such as wastewater, with bio-electrochemical reduction of inorganic carbon compounds, the inventors were able to convert influent comprising organic compounds present in an aqueous liquid stream, such as wastewater, and a gaseous or aqueous syngas stream comprising inorganic carbon compounds into an effluent comprising short chain organic molecules in a single biofilm bioreactor comprising electrodes.

As referred to herein "organic compounds present in an aqueous liquid stream" refers to an aqueous organic compound-containing stream typically being an industrial wastewater with a high solid content (e.g. organic sludge) or a wastewater with low solid contents. The aqueous liquid streams which may be treated in the process as described herein and the organic compounds contained in such streams may vary widely. Illustrative of such pollutants are lipids and organic polymers such as polypeptides and carbohydrates including for instance cellulose or derivatives thereof and inorganic pollutants such as hydrogen sulfide and ammonia. In the preferred embodiments of this invention the pollutants are those which are common in waste streams from industrial manufacturing facilities. This is not to say that the process can or must be practiced only on such streams. The process which is the invention herein may be practiced on any aqueous feed containing levels of organic and inorganic pollutants which are to be reduced.

The initial concentration of organic pollutants contained in the aqueous waste stream used in the process as described herein may vary widely. The pH of the aqueous organic pollutant-containing stream may need to be adjusted for optimum treatment. In the preferred embodiments of the invention, the pH of the feed is from about 4.0 to about 9.0, preferably from about 6.0 to about 8.0 and in the most preferred embodiment of the invention, the pH of the feed is from about 6.5 to about 7.5.

Additional nutrients may also be provided. Additional nutrients may be added through use of known additives such as composition comprising biologically usable N, P and K containing chemicals, trace elements such as metals, vitamins or other known nutrients for microorganisms. In particular said nutrients may be added in the form of commercially available fertilizers. Usually sufficient amounts of nutrients are present in the aqueous organic pollutant-containing stream to satisfy minimum requirements of the microorganisms present in the bioreactor but in order to be able to treat a wide variety of aqueous organic pollutant-containing streams, in certain cases additional nutrients may need to be added.

As referred to herein "inorganic carbon compounds" refer to inorganic chemical molecules comprising carbon but lacking carbon-hydrogen bonds. Preferably said inorganic carbon compounds are C-1 inorganic carbon compounds preferably chosen from $$CO_2, CO, HCO_3^-, \text{ and } CO_3^{2-}.$$

As referred to herein "short chain organic molecules" typically refer to C1 to C6 hydrocarbons or derivatives thereof, in particular C1 to C4 hydrocarbons, C1 to C4 carboxylic acids and/or C1 to C4 aliphatic alcohols.

As referred to herein "electrochemical oxidation" refers to the process where as a result of the application of a controlled voltage to the electrodes micro-spaces and micro-conditions of higher redox-potential will be created at the anode which will provide in the oxidation of "difficult to break" organic compounds that otherwise will pass undegraded in a biological treatment process, such as anaerobic digestion. This electrochemical oxidation may occur with or without the involvement of biological reactions (in a biofilm on the anode). Larger organic molecules will produce more carbon dioxide, protons and electrons, needed at the cathode, as indicated in the general Equation 1.

$$C_nH_{2n+1} - COOH + [2(n+1) - 2]H_2O \rightarrow \tag{1}$$

$$(n+1)CO_2 + (6n+2)H^+ + (6n+2)e^{-1}$$

As referred to herein "bio-electrochemical reduction" refers to the process at the cathode where due to the application of a controlled voltage to the electrodes in an anaerobic digestion environment, micro-spaces and micro-conditions at the cathode will result in the reduction of inorganic carbon thereby generating at the cathode short chain organic molecules such as for instance methane (equation 2) or acetic acid (equation 3).

$$8H^+ + CO_2 + 8e^- \rightarrow CH_4 + 2H_2O \qquad (2)$$

$$8H^+ + 2CO_2 + 8e^- \rightarrow C_2H_4O_2 + 2H_2O \qquad (3)$$

As referred to herein "biofilm bioreactor" refers to a reactor comprising microorganisms growing in a biofilm on surfaces, being electrode surfaces in the present invention.

Accordingly, the present invention provides in a method for converting one or more influent streams comprising organic compounds present in an aqueous liquid stream, such as wastewater, and a gaseous or aqueous syngas stream comprising inorganic carbon compounds, preferably C-1 inorganic carbon compounds such as $$CO_2, CO, HCO_3^-, \text{ and } CO_3^{2-},$$

into an effluent stream comprising short chain organic molecules, such as C1 to C6 hydrocarbons or derivatives thereof, in particular C1 to C4 hydrocarbons, C1 to C4 carboxylic acids and/or C1 to C4 aliphatic alcohols, in an biofilm bioreactor comprising electrodes, said method comprising:

the electrochemical oxidation of said organic compounds, thereby forming inorganic carbon compounds; and;

the bio-electrochemical reduction of said inorganic carbon compounds, thereby forming short chained organic molecules (such as methane or acetic acid);

characterized in that said bioreactor is an anaerobic bioreactor comprising a biofilm growing on the cathodes and optionally the anodes as well as microorganism in suspension.

The processes occurring in the single bioreactor according to the present invention occur simultaneously in a single tank or chamber of the bioreactor.

In particular embodiments the method as disclosed herein further provides in the bio-electrochemical oxidation of organic compounds, in particular using biological reactions with the microorganisms present in a biofilm on the anode.

It has been found that the combination of electrochemical oxidation and bio-electrochemical reduction can occur in the same single chamber bioreactor by working in anaerobic conditions and using microorganisms in suspension as well as a biofilm growing on the cathodes and optionally the anodes in the bioreactor. By providing voltage to the electrodes degradation of complex organic molecules into inorganic carbon pounds at the anode can be combined with the formation of short chain organic molecules at the cathode from inorganic carbon compounds. The combination of electrodes and microorganisms allow for an enhancement of the oxidation of the organic compounds which can subsequently be reduced to form short chain organic molecules.

In particular embodiments the one or more influent streams comprising organic compounds present in an aqueous liquid stream are wastewater streams comprising organic compounds such as industrial effluent or other sources of wastewater.

In particular embodiments the influent stream is the bulk water of an anaerobic digester comprising organic compounds and dissolved carbon dioxide generated in the anaerobic digestion process. Said organic compounds are oxidized at the anode and dissolved carbon dioxide is reduced to methane at the cathode. The treated effluent may be returned to the anaerobic digester.

In particular embodiments the one or more influent streams comprise an aqueous liquid stream, such as a wastewater stream, comprising organic compounds as well as a gaseous or aqueous syngas and/or carbon dioxide stream comprising inorganic carbon compounds.

As referred to herein the term "syngas" refers to a synthesis or fuel gas mixture consisting primarily of hydrogen, carbon monoxide, and very often some carbon dioxide and methane. Syngas may be produced from many sources, including natural gas, coal, biomass, or virtually any hydrocarbon feedstock, by reaction with steam (steam reforming), carbon dioxide (dry reforming) or oxygen (partial oxidation). In particular embodiments that syngas is obtained from the pyrolysis and gasification of organic matter.

The syngas as referred to herein may be added to the bioreactor as a gaseous or aqueous stream. In case the syngas stream is a gaseous stream, solubilization of the syngas into an aqueous phase may be required prior to it entering into the bioreactor. Solubilization of the syngas allow a rapid oxidation and neutralization of the radicals present in the syngas, thereby removing compounds which might potentially be harmful for the microorganisms present in the bioreactor. Adding the syngas into an aqueous phase further enables anaerobic organisms such as homoacetogens to convert inorganic carbon molecules to short chain organic molecules such as acetate.

In a particular embodiment, the method as disclosed herein treats a carbon dioxide stream such as a carbon dioxide stream from a carbon capture plant or from an industrial process generating carbon dioxide according to the same principles as described for "syngas".

In a particular embodiment, the method as disclosed herein provides in that the effluent stream of the bioreactor is biogas, in particular a biogas comprising methane.

As referred to herein the term "biogas" refers to the gas produced by the bioreactor according to the invention. The biogas primarily consists of methane and carbon dioxide.

Compared to other ways for producing biogas, the method and apparatuses described herein are able to generate a biogas with higher methane content than that obtained for a given feed with anaerobic digestion alone by converting some of the anaerobic digestion generated carbon dioxide to methane thereby also increasing the total amount of methane generated from the given feed. Thus at least 20% of the carbon dioxide content in the biogas can be converted to methane, in particular 50% or more, and more in particular 80% or more, implying that the methane content of the biogas can be 90% or more. This represents an upgrade of the biogas in an integrated process as opposed to standard downstream biogas upgrading by methane and carbon dioxide separation.

Accordingly, where the typical methane content in biogas obtained from conventional system ranges between 50% and 70%, the method and apparatuses as described herein are able to generate a biogas with higher methane content, in particular a biogas comprising at least 75% methane, in particular at least 80% methane, more in particular at least 85% methane, and preferably at least 90% methane.

Alternatively, the method and apparatuses described herein can be used to produce an effluent comprising short chain organic molecules, such as C1 to C4 hydrocarbons, C1 to C4 carboxylic acids and/or C1 to C4 aliphatic alcohols other than methane. These other short chain organic molecules may include formic acid, acetic acid, oxalic acid, glyoxylic acid, glycolic acid, propionic acid, acrylic acid, propiolic acid, malonic acid, tartronic acid, mesoxalic acid, dihydroxymalonic acid, pyruvic acid, lactic acid, hydracrylic acid, glyceric acid, glycidic acid, butyric acid, isobutyric acid, alpha-ketobutyric acid, acetoacetic acid, succinic semialdehyde, fumaric acid, maleic acid, acetylenedicarboxylic acid, oxaloacetic acid, malic acid, tartaric acid, crotonic acid, methanol, ethanol, propanol, butanol and/or isobutanol. In particular the produced effluent comprises acetic acid.

In a particular embodiment, the method as disclosed herein provides in that the bioreactor is operated at a pressure above 1.0 bar, in particular at a pressure of about 1.5 bar, more in particular at a pressure of about 2.0 bar. The bioreactor is typically operated at a pressure below 3.0 bar. By working at an overpressure an increase in mass transfer and solubility of the gases was observed, thereby rendering the reaction process more efficient.

In a particular embodiment, the method as disclosed herein provides in that the electrodes comprise of anodes and cathodes arranged in a surface area to volume ratio of at least 5 $m^2/m^3$, in particular at least $m^2/m^3$, in particular at least 15 $m^2/m^3$ and in particular at least 20 $m^2/m^3$, thereby maximizing the electrode area efficiency and biofilm development. Working at an optimal surface area to volume ratio influences the coulombic efficiency.

Figure 2:
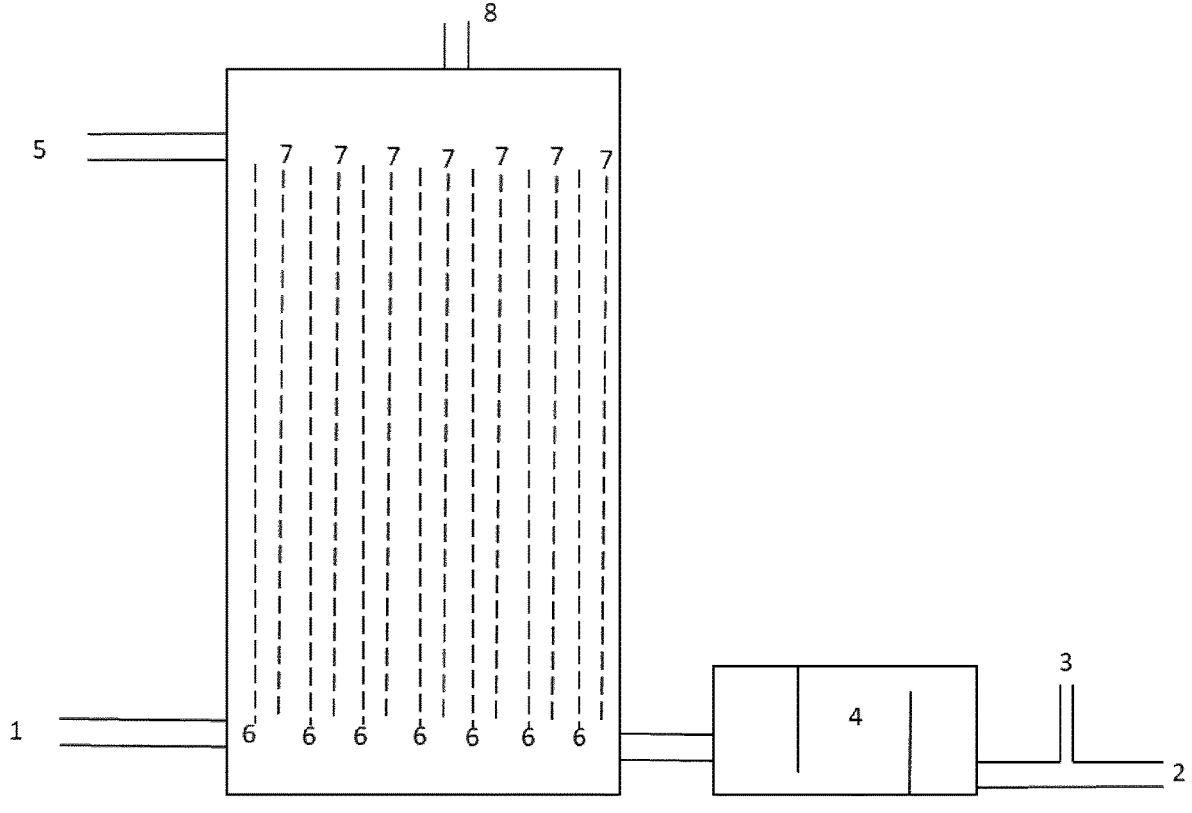
FIG. 2 shows a bioreactor with a vertical arrangement of electrodes according to the present invention.

In particular embodiments the electrodes comprise anodes and cathodes which are alternatingly stacked horizontally (FIG. 1) or vertically (FIG. 2) within said bioreactor.

As referred to herein "alternating stacking" refers to a repetitive stacking of anodes (A) and cathodes (C). Several sequences may be considered, such as for instance CACACAC, CAACAAC, or others.

In a particular embodiment, the method as disclosed herein provides in that method further comprises the step of introducing, solubilizing and/or pre-fermenting the syngas with homoacetogenic bacteria prior to it entering into said bioreactor. The pre-fermentation allows for a partial breakdown of the compounds present in the syngas that can harm microorganisms, such as oxidizing agents, prior to it entering into the bioreactor.

In a particular embodiment, the method as disclosed herein provides in that homoacetogenic bacteria suspended or at the electrodes as a biofilm, feed on the inorganic carbon and hydrogen gas to produce an array of organic compounds until a thermodynamic barrier is reached, the application of a voltage on the electrodes allows for this barrier to be broken or moved and the enhanced electron and proton transfer allows further conversion reactions such as of the inorganic carbon molecules into short chain organic molecules.

In a particular embodiment, the method as disclosed herein provides in that a biofilm growing on the cathodes and optionally the anodes enables efficient retention and high concentration of active biomass thereby rendering sludge retention time much longer than hydraulic retention time, allowing high hydraulic loads. By having a biofilm growing on the cathodes and optionally the anodes, a high density active biomass reactor is created resulting in a compact process that is able to withstand changes in mass and hydraulic loads. Furthermore biofilm treatment systems are more resistant to toxic elements, as toxic substances diffuse slowly to the deeper layer of biofilm allowing a gradual acclimatization, as the deeper layer of biofilm are exposed to less concentrated levels of toxic substances. A further benefit is that there is an increased biological activity compared to suspended sludge systems because more protection for the microorganisms is given in the biofilm. The biofilm growing on the electrodes are especially efficient since the electrodes enhance the transfer of electrons to or from organisms, serving as electron donor or electron acceptor to overcome rate limiting barriers.

In a particular embodiment, the method as disclosed herein provides in that the microorganisms enhance the oxidation of organic matter to products that can further be reduced to short chained organic compounds through both heterotrophic and autotrophic methanogenesis.

Furthermore, the archaea culture in biofilm growing on the cathode will allow the formation of methane gas from $H^+$, electrons and $$CO_2/HCO_3^-$$

through the biologically mediated process of hydrogenotrophic methanogenesis. Further, the archaea culture in biofilm growing on electrodes will allow the formation of methane gas from $H_2$ gas and $$CO_2/HCO_3^-$$

through the archaea mediated process of hydrogenotrophic methanogenesis. Further biofilm growing in suspension and on electrodes will allow the formation of methane from acetic acid through the archaea mediated process of acetoclastic methanogenesis.

In a particular embodiment, the method as disclosed herein provides in that said bioreactor is an up-flow, plug-flow or countercurrent bioreactor. In particular said bioreactor is an Up-flow Anaerobic bed reactor, such as an Up-flow Anaerobic Sludge Bed (UASB) reactor. It has been found that by using an UASB bioreactor in particular the reaction rate in the suspended phase could be increased and can enhance mass transfer between liquid phase and biofilm.

Compared to other types of bio-electrochemical bioreactors it has been found that the method as described herein does not require the presence of a membrane inside the bioreactor to separate chambers for anode and cathode. The absence of any membrane in the reactor renders the process more reliable and less prone to malfunctions. Accordingly, in the method as provided herein a single bioreactor is used for the occurring reactions and said single bioreactor comprises is a single chamber, therefore said single bioreactor does not comprise a membrane dividing the single bioreactor in multiple chambers.

In a particular embodiment, the method as disclosed herein provides in that the voltage applied to the electrodes for the electrochemical oxidation and bio-electrochemical reduction ranges between 250 mV and 1200 mV vs. SHE at the cathode. Depending on the voltage applied to the electrodes the type of reaction that occurs may be altered. For instance, the reaction in driven towards the generation of methane by applying a voltage of about 450 mV vs. SHE at the cathode, while the generation of acetic acid can be obtained by applying a voltage of about 650 mV vs. SHE at the cathode. In a particular embodiment the voltage applied to the cathodes and anodes is different, allowing enhanced production rates and product yields.

In a particular embodiment the method as described herein in characterized in that the voltage applied to the electrodes for the electrochemical oxidation and bio-electrochemical reduction at the cathode is regulated to obtain certain products.

In a particular embodiment, the method as disclosed herein provides in that the suspension in the bioreactor is characterized by having a low oxidation reduction potential (ORP), preferably ranging between −250 and −450 mV, more preferably ranging between −350 and −400 mV.

In a particular embodiment, the method as disclosed herein provides in that the method further comprises the step of adding an aqueous nutrient solution to the influent.

Since microbial activity of both the anaerobic microorganisms growing on the electrodes and suspended demands nutrients, and some industrial wastewaters lacks sufficient nutrients for the required biomass growth (in case of the invention is applied to such industrial wastewater lacking nutrients), these nutrients have to be added separately. Therefore, in a favourable embodiment of a process according to the invention, the process comprises the step of adding an aqueous nutrient solution to the feed stream.

In a particular embodiment, the method as disclosed herein provide in that the effluent biogas and/or the sludge/wastewater exiting the bioreactor are recycled to an upstream or downstream processing facility.

In a further aspect, the present invention relates to a single anaerobic bioreactor for performing the method as disclosed herein, comprising a biofilm growing on the cathodes and optionally the anodes as well as microorganisms in suspension, wherein said bioreactor is a single chamber stand-alone bioreactor or a single chamber add-on bioreactor (e.g. to existing waste handling processes to boost methane yield in existing biogas plants).

In a particular embodiment, the bioreactor as disclosed herein provides in that said bioreactor does not comprise a membrane to divide the bioreactor in multiple chambers.

In a particular embodiment, the bioreactor as disclosed herein provides in that said bioreactor is an up-flow, plug-flow or countercurrent bioreactor. In particular said bioreactor is an Up-flow Anaerobic Bed reactor, such as an Up-flow Anaerobic Sludge Bed (UASB) reactor. It has been found that by using an UASB bioreactor in particular the reaction rate in the suspended phase could be increased.

In a particular embodiment, the bioreactor as disclosed herein provides in that the electrodes comprise of anodes and cathodes arranged in a surface area to volume ratio of at least 5 $m^2/m^3$, in particular at least $m^2/m^3$, in particular at least 15 $m^2/m^3$ and in particular at least 20 $m^2/m^3$, thereby maximizing the electrode area efficiency and biofilm development. Working at an optimal surface area to volume ratio influences the coulombic efficiency.

In particular embodiments the electrodes comprise anodes and cathodes which are alternatingly stacked horizontally (FIG. 1) or vertically (FIG. 2) within said bioreactor.

In a further aspect the present invention provides in the use of electrochemistry and microbial biological reactions in biofilm growing on the cathodes and optionally the anodes and microorganisms in suspension to convert one or more influent streams comprising organic compounds in an aqueous liquid stream, such as wastewater, and a gaseous or aqueous syngas stream comprising inorganic carbon compounds into an effluent stream comprising short chain organic C1 to C6 hydrocarbons or derivatives thereof.

It has further been found that the methods and apparatuses as described herein also enable the oxidation of ammonium, ammonia and sulfides present in an aqueous liquid stream entering the bioreactor.

The methods and apparatuses of the present invention have also been found to be able to remove sulfides ($S^{2-}$/$HS^-$/$H_2S$) from the aqueous liquid stream entering the bioreactor. In particular embodiments this is achieved by oxidation reactions at the anode.

It has been found that the controlled voltage to the electrodes in an anaerobic bacterial environment further allows the oxidation of sulfides to release electron equivalent at the anode to produce Sulphur (Equation 4) and/or sulfate (Equation 5). Electrons and protons thereby made available at the anode will be driven to the cathode for the production of organic molecules by reduction of inorganic carbon.

$$HS^- \rightarrow S^0 + H^+ + 2e^- \qquad (4)$$

$$HS^- + 4H_2O \rightarrow SO_4^{2-} + 9H^+ + 8e^- \qquad (5)$$

Reject water in biogas plants (wastewater stream after centrifugation of digested sludge), bulk liquid of anaerobic digestion processes and many other domestic and industrial wastewaters are also rich in ammonium. This supposes an environmental challenge as ammonium is a contaminant that can cause eutrophication in recipient water bodies. In sludge treatment systems at wastewater treatment plants, ammonium rich reject water usually goes back to the main treatment plant inlet, often causing great imbalances, process disturbances and challenges. Ammonium can be removed by energy intensive, extensive treatment systems that includes the steps of nitrification and denitrification, such as the compact Anammox process.

It has been found that the controlled voltage to the electrodes in an anaerobic bacterial environment further allows the oxidation of ammonium to release electrons and protons at the anode to produce nitrogen gas (Equation 6). Electrons and protons thereby made available at the anode will be driven to the cathode to achieve Equation 2, resulting in the stoichiometrically equivalent Equation 7.

$$2NH_4^+ = N_2 + 8H^+ + 6e^- \qquad (6)$$

$$8NH_4^+ + 3CO_2 \rightarrow 4N_2 + 3CH_4 + 6H_2O + 8H^+ \qquad (7)$$

Electrochemical oxidation of inorganic components, such as ammonium and hydrogen sulfide, as a result of the application of a controlled voltage at the anode will also produce protons and electrons that can be used at the cathode (e.g. equation 2).

In particular embodiments, the method as disclosed herein further provides in the electrochemical oxidation of inorganic compounds, in particular the electrochemical oxidation of hydrogen sulfide and/or ammonium.

In particular embodiments, the method as disclosed herein further provides in the bio-electrochemical oxidation of inorganic compounds, in particular the bio-electrochemical oxidation of hydrogen sulfide and/or ammonium.

EXAMPLES

Figure 3:
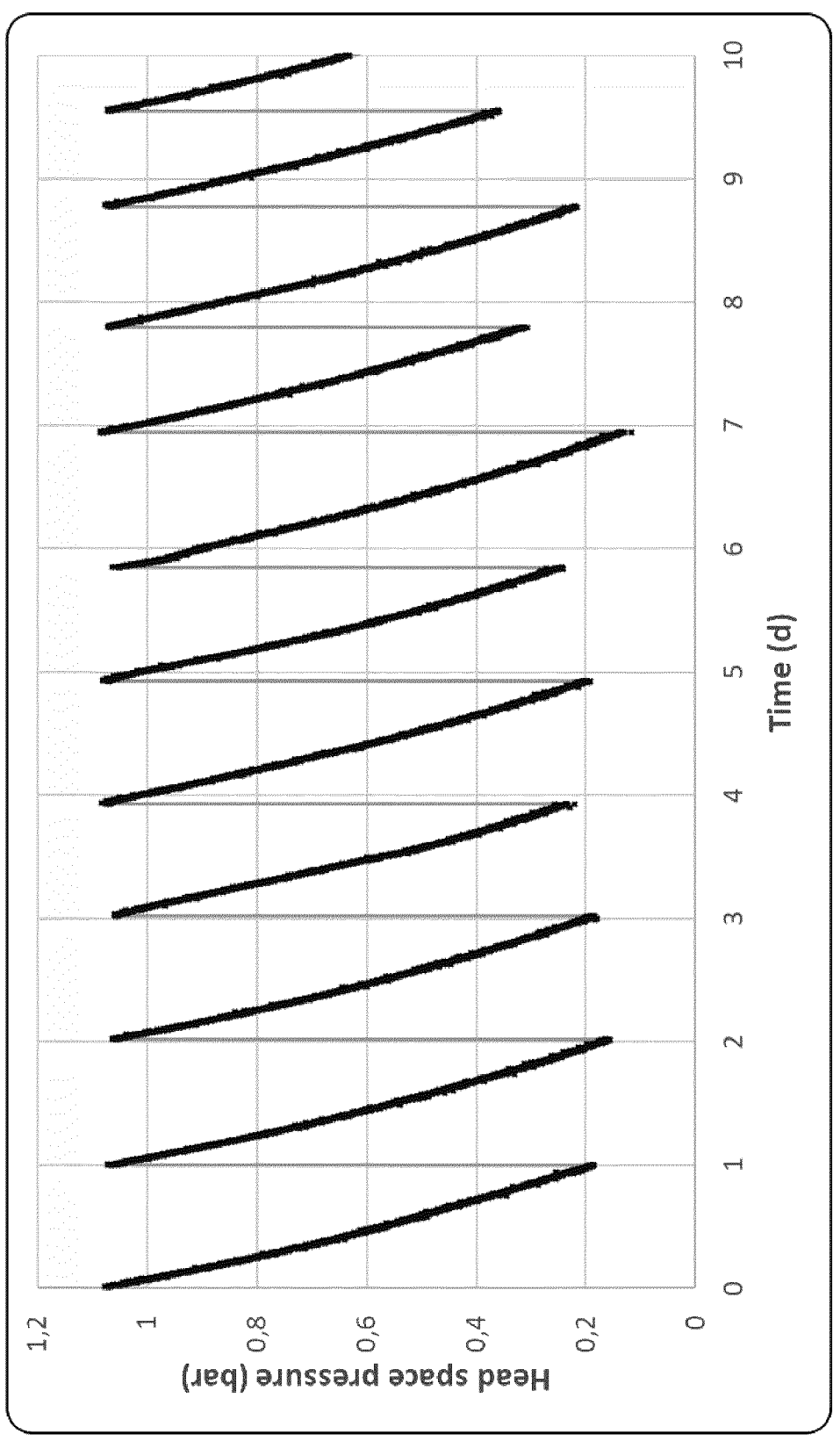
FIG. 3 shows an example of a reactor running at 1 bar $H_2$ overpressure, which offers a consistent pressure drop.

The method as described herein was performed on a laboratory scale where several laboratory scale reactors (according to the present invention) run continuously and semi-continuously at varying hydraulic retention times ranging between 3-24 hours. Reject water (polluted water after sludge dewatering) was fed to the reactors and have shown biogas production with 80-96% methane content, sulfide removal 50-99% and ammonia removal 5-25%. The reactors were fed syngas fed-batch wise, with varying headspace pressure 1-3 bars. The reactors were pressurized and re-pressurized after headspace pressure dropped to close to zero bar overpressure. Hydrogen gas pressure, which has limited solubility, was consumed at a rate of 18-48 mmol $H_2$/Ld. FIG. 3 shows an example of a reactor running at 1 bar $H_2$ overpressure, which offers a consistent pressure drop.

The invention claimed is:

1. A method for converting one or more influent streams into an effluent stream comprising short chain organic C1 to C6 hydrocarbons or derivatives thereof in a single anaerobic bioreactor comprising electrodes;

wherein the one or more influent streams comprise a wastewater stream comprising organic compounds and a gaseous or aqueous syngas stream comprising inorganic carbon compounds consisting primarily of hydrogen and carbon monoxide, and optionally one or both of carbon dioxide and methane;

wherein the wastewater stream and the syngas stream are introduced separately or are pre-combined prior to introduction into the single anaerobic bioreactor; and wherein said single anaerobic bioreactor comprises bio-films growing on cathodes and optionally on anodes, as well as microorganisms in suspension;

said method comprising:

electrochemical oxidation of said organic compounds, thereby forming inorganic carbon compounds; and bio-electrochemical reduction of said inorganic carbon compounds, thereby forming short chained organic C1 to C6 hydrocarbons or derivatives thereof;

wherein said method further comprises solubilizing the syngas and/or pre-fermenting the syngas with homo-acetogenic bacteria prior to said syngas entering into said single anaerobic bioreactor.

2. Method according to claim 1 wherein said single anaerobic bioreactor does not comprise a membrane to divide the single anaerobic bioreactor into multiple chambers.

3. Method according to claim 1 further comprising:

bio-electrochemical oxidation of organic compounds using biological reactions with the microorganisms present in a biofilm on the anode;

electrochemical oxidation of inorganic compounds, including electrochemical oxidation of hydrogen sulfide and/or ammonium; and/or bio-electrochemical oxidation of inorganic compounds, including bio-electrochemical oxidation of hydrogen sulfide and/or ammonium.

4. Method according to claim 1, wherein said effluent stream of said single anaerobic bioreactor is biogas comprising methane.

5. Method according to claim 1, wherein the single anaerobic bioreactor is operated at an absolute pressure between 1.0 and 3.0 bar.

6. Method according to claim 1, wherein the electrodes comprise said anodes and cathodes arranged in a surface area to volume ratio of at least 5 $m^2/m^3$.

7. Method according to claim 1, wherein the electrodes comprise anodes and cathodes which are alternatingly stacked vertically or horizontally within said single anaerobic bioreactor.

8. Method according to claim 1, wherein said single anaerobic bioreactor is an Up-flow Anaerobic Bed reactor.

9. Method according to claim 8, wherein the Up-flow Anaerobic Bed reactor is an Up-flow Anaerobic Sludge Bed (UASB) reactor.

10. Method according to claim 1, wherein the voltage applied to the electrodes for the electrochemical oxidation and bio-electrochemical reduction ranges between 250 mV and 1200 mV vs. standard hydrogen electrode (SHE) at the cathode.

11. Method according to claim 1, wherein the suspension in the single anaerobic bioreactor has a redox potential between −250 and −450 mV.

12. Method according to claim 1, wherein the method further comprises the step of adding a nutrient solution to the influent.

* * * * *